United States Patent [19]
Kraus et al.

[11] Patent Number: 4,966,163
[45] Date of Patent: Oct. 30, 1990

[54] EXTENDABLE GUIDEWIRE FOR VASCULAR PROCEDURES

[75] Inventors: Jeffrey L. Kraus, San Jose; Linda T. Guthrie, Fremont, both of Calif.

[73] Assignee: Advanced Cardiovascular Systems, Inc., Santa Clara, Calif.

[21] Appl. No.: 311,005

[22] Filed: Feb. 14, 1989

[51] Int. Cl.$^5$ ............................................. A61B 5/00
[52] U.S. Cl. ................................... 128/772; 403/77
[58] Field of Search .................... 128/772, 656–658, 128/341, 344; 604/164, 166, 170, 282; 403/1, 76–77, 118, 296, DIG. 4; 285/330, 390

[56] References Cited

U.S. PATENT DOCUMENTS

| | | | |
|---|---|---|---|
| 2,708,591 | 5/1955 | Schiesel | 403/77 X |
| 3,143,365 | 8/1964 | Egger | 403/77 |
| 3,406,992 | 10/1968 | Grotness | 403/77 X |
| 3,497,248 | 2/1970 | Teramachi | 403/77 |
| 4,827,941 | 5/1989 | Taylor et al. | 128/657 |
| 4,875,489 | 10/1989 | Messner | 128/772 |

FOREIGN PATENT DOCUMENTS 2180454 4/1987 United Kingdom ............... 128/772

Primary Examiner—Max Hindenburg
Attorney, Agent, or Firm—Fulwider, Patton, Lee & Utecht

[57] ABSTRACT

An extendable guidewire system for introducing a dilatation catheter into the arterial system of a patient. The guidewire system has guidewire and extension sections with a connection therebetween which permits the two sections to be joined together and separated simply by twisting the two sections to effect a threaded connection. One of the sections can be used for positioning the catheter within the cardiovascular system, and the other section an be employed to extend the wire to change catheters.

4 Claims, 1 Drawing Sheet

U.S. Patent
Oct. 30, 1990
4,966,163
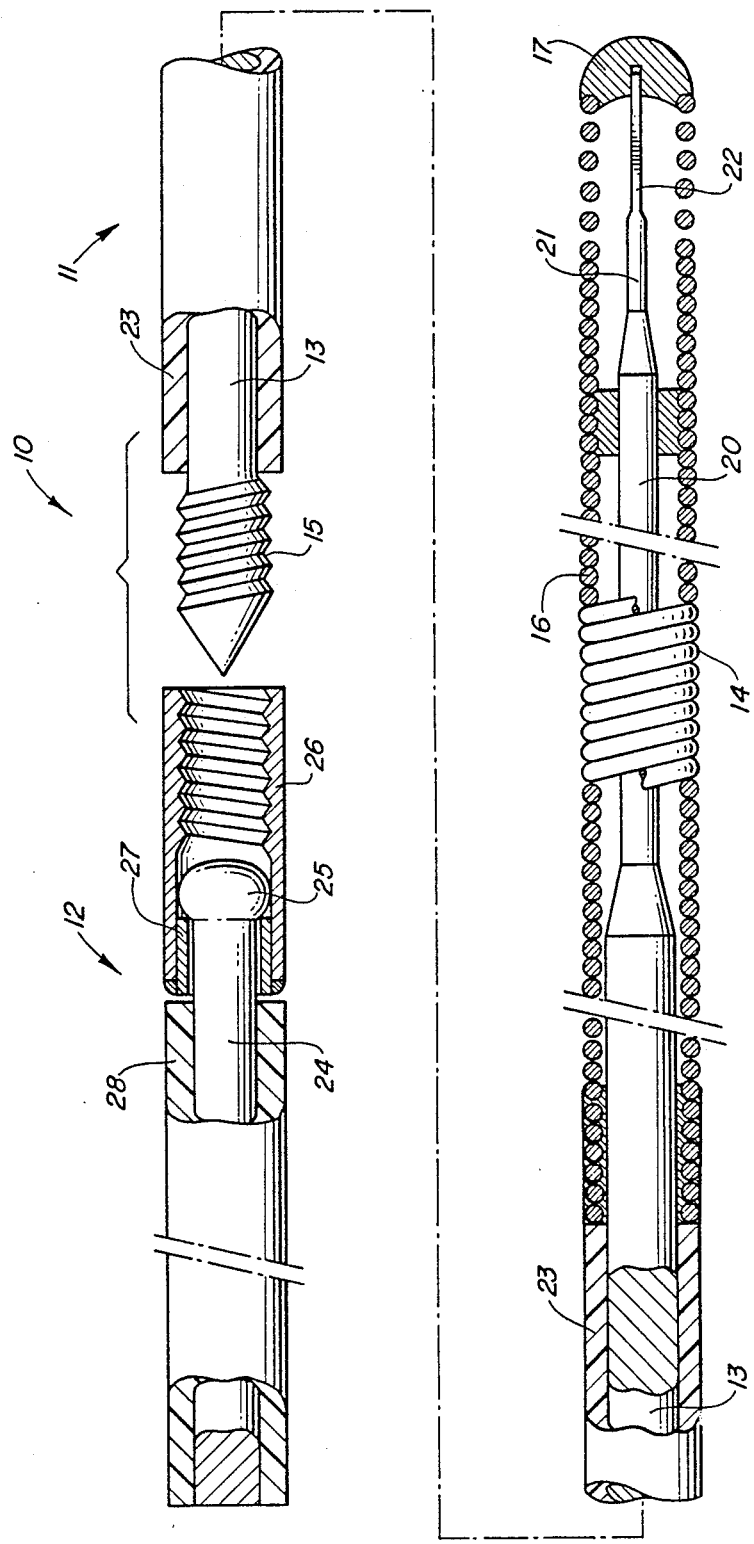

EXTENDABLE GUIDEWIRE FOR VASCULAR PROCEDURES

BACKGROUND OF THE INVENTION

This invention generally relates to vascular procedures such as angioplasty, and more particularly to an extendable guidewire for use in such procedures.

Guidewires are currently used to facilitate the placement of catheters in the arterial system of a patient for cardiovascular procedures such as angioplasty. The guidewire is typically on the order of 20-50 cm longer than the catheter to permit the guidewire and the catheter to be advanced relative to each other as they are steered into position within the patient's body. Suitable guidewires are described in U.S. Pat. No. 4,538,622 (Samson et al.) and U.S. Pat. No. 4,569,347 (Frisbie) which are hereby incorporated herein in their entirety.

If the deflated balloon on the dilatation catheter is too large to pass through a stenosis, then the catheter must be exchanged for one having a lower deflated profile. In the usual procedure to change catheters, the guidewire is removed from the patient, and an exchange wire is inserted in its place. The in-place catheter is then removed from the patient and a new catheter is inserted into the patient over the exchange wire. The exchange wire is then removed an the guidewire is reinserted. The exchange wire is substantially longer than the guidewire, and it generally extends outside the patient's body for a distance greater than the length of the catheter. With a dilatation catheter having a length on the order of 80 cm, for example, a guidewire might have a length on the order of about 100 to 175 cm, and an exchange wire might have a length on the order of about 200 to 300 cm. The use of an exchange wire has the obvious disadvantage that it complicates the angioplasty procedure.

Heretofore, there have been some attempts to eliminate the need for a separate exchange wire by attaching an extension wire to a guidewire to extend the length thereof. The two wires are joined together by a crimped connector which requires a special tool. Once the wires have been crimped, the connection therebetween is permanent, and the extension wire cannot be removed except by severing it from the guidewire. Prior extendable wires for use in coronary angioplasty procedures have been found to be no very suitable in peripheral arteries because the connections are not strong enough.

What has been needed and heretofore unavailable is a strong guidewire extension which can be readily connected and disconnected to the guidewire when it is in position within the patient. The present invention satisfies this need.

SUMMARY OF THE INVENTION

The present invention provides a new and improved guidewire system which is particularly suitable in peripheral arteries and the method of using the same.

In accordance with the present invention, a guidewire is provided with main and extension sections which are detachably secured together by means of a threaded fitting. One of the guidewire sections has a threaded female portion at the connected end thereof, and the other guidewire section has a threaded male connecting end portion which can be threaded into the threaded female portion, preferably either or both of the threaded members are mounted to be freely rotatable about the longitudinal axis of the guidewire section to which they are connected. The two sections can readily be connected and disconnected during the procedure.

In the presently preferred embodiment, the female end of the connection is rotatably mounted to facilitate the connection.

These and other advantages of the invention will become more apparent from the following detailed description thereof and the accompanying exemplary drawings.

BRIEF DESCRIPTION OF THE DRAWINGS

The FIGURE is a fragmentary, elevational view, partially in section, of an extendable guidewire system embodying features of the invention, with parts separated.

DETAILED DESCRIPTION OF THE INVENTION

As illustrated in the FIGURE, the guidewire system 10 embodying features of the invention has a main section 11 which is adapted to be inserted into a patient's vascular system and an extension section 12 which can be connected and disconnected to the main section 11 to facilitate the exchange of catheters without the need for removing the main section 10 from the patient's vascular system. Main guidewire 11 generally comprises an elongated shaft 13 with a flexible distal end 14 and a threaded male portion 15 at its proximal end. The flexible tip 14, shown generally, has a helical coil 16 and a rounded distal tip 17. The elongated shaft 13 tapers to smaller diameter sections 20 and 21 and a last section 22 which is preferably flat. The length of the shaft 13 is covered with polyethylene coating 23, as shown, up to the coil 16.

Extension section 12 has an elongated shaft 24 with an enlargement 25 at its distal end. A freely rotatable internally threaded female connection member 26 is secured to the distal end of extension 12 by means of an internal collar 27 bonded thereto. The collar 27 has an internal diameter less than the maximum radial dimension of the enlargement 25 but larger than the end of section 12 proximal to the enlargement to facilitate the rotation of female member 26 independent of shaft 24. The enlargement 25 can be suitably made such as by forming a weld ball on the distal end of shaft 24. The portion of the shaft 24 proximal to the female member 26 is covered with a plastic coating 28.

The main guidewire section 12 is intended for use in positioning a dilatation catheter (not shown) in the arterial system of a patient, and it has a length corresponding to the length of a conventional guidewire for this purpose. Details of typical dilatation catheters and guidewires can be found in the patents cited previously and incorporated herein.

Extension section 12 is sufficiently long so that when the guidewire sections 11 and 12 are connected together, the guidewire system 10 has an overall length suitable for exchanging catheters without removing the main section 11 from the patient's vascular system. With a dilatation catheter having a length on the order of 90-130 cm, for example, section 11 might have a length of 110-150 cm, and section 12 might have a length of 100-130 cm.

Shafts 13 and 24 and female member 26 can be fabricated from suitable material, such as stainless steel, nitinol (55% Ni-Bal. Ti) or other suitable material, and each should have a diameter to allow a dilatation catheter to pass freely over them. Preferably, the two shafts 13 and 24 are provided with a smooth transition between them. Either or both of the shafts can be provided with a coating of polyethylene or polytetrafluoroethylene, which is sold under the trademark Teflon by the DuPont Corporation, or another suitable material.

Typical dimensions of the main guidewire section include a diameter of the shaft 13 of about 0.020 inch, the small diameter section 20 about 0.008 to about 0.015 inch in diameter and about 17 cm long, the small diameter section 21 about 0.004 inch in diameter and about 2 cm long and the flattened section 22 about 0.001 to 0.003 inch thick and about 3 cm long. The coil 16 may be made of Teflon coated stainless steel wire about 0.007 inch in diameter and, preferably, the distal section thereof is prestretched, as shown. All or a portion of the coil 16 may be formed of more radiopaque material, such as platinum, titanium, palladium and alloys thereof. The proximal end of the coil 16 is preferably bonded to the shaft 13 by a suitable adhesive such as a cyanoacrylate. The polyethylene coating 23 on the shaft 13 is about 0.007 inch thick to provide a smooth transition to the coil 16. The threaded male member 15 is about 0.5 to about 2 cm long and about 0.022 inch in maximum diameter. The distal tip is pointed to aid in entry and has a diameter which facilitates the threaded connection with the female member 26.

Typical dimensions of the extension section include a diameter of about 0.015 to 0.02 inch with a polyethylene coating thereon of about 0.007 inch thick. The threaded female member is about 3 cm long and about 0.035 inch in outer diameter.

In use, the main guidewire section 11 is percutaneously introduced into the vascular system of a patient with a dilatation catheter through an introducer (not shown). The distal tip of the guidewire is advanced beyond the distal tip of the dilatation catheter while the latter is held in place. The main guidewire section 11 is advanced into the selected artery. The guidewire tip is preferably advanced through the lesion and beyond it, in order to permit the balloon portion of the dilatation catheter to be positioned within the lesion over a more supportive section of the guidewire. Once in position, the main guidewire section 11 is held in place and the dilatation catheter is advanced along it until the inflatable balloon thereof is within the lesion. Threaded male end portion 15 remains outside the patient's body and outside any adapter which may be connected to the proximal end of the dilatation catheter.

To exchange catheters, the main guidewire section 11 is extended by manually threading the rotatable female tubular member 13 on the threaded male member 15 on the distal end of extension section 12. When the two guidewire sections are threadably connected together, the dilatation catheter can then be withdrawn from the patient's body over the extended guidewire system.

A new dilatation catheter may then be introduced over the extension section 12 and advanced along the main guidewire section 11 within the patient's body until the balloon crosses the lesion. Once the proximal end of the new balloon catheter has advanced beyond the threaded connection between female member 26 and male member 15, section 12 can be removed by rotating the female member 26 and then pulling the two sections apart without disturbing the position of the main section 11 in the patient's body.

The invention has a number of important features and advantages. The two sections of the guidewire can be connected together whenever a longer wire is needed, and they can be separated whenever the additional length is not required. The two sections of the guidewire may be connected and disconnected by the physician by simply rotating the threaded female member. This can be done as needed, and no special tools are required wither to make the connection or to separate it. Thus, the catheter exchange is greatly simplified. The threaded connection provides the strength frequently needed in peripheral procedures.

It is apparent from the foregoing that a new and improved extended guidewire system has been provided. While the present invention has been described herein with the tubular connecting element fixed to the distal end of the main guidewire section and the male member adapted to be inserted into the open end of the tubular member on the distal end of the extension section, it is obvious that the female connector member and male connector member may be interchanged. Moreover, it will be apparent to those familiar with the art that other modifications and improvements can be made without departing from the scope of the invention as defined by the following claims.

What is claimed is:

1. An extendable intravascular guidewire system which facilitates the insertion and withdrawal of an intravascular catheter from a patient, comprising:
   (a) a main elongated guidewire section adapted to be inserted into a patient's vascular system which has a mating end adapted to extend out of the patient;
   (b) an elongated guidewire extension section having a
   (c) a manually operable, releasable connection between the mating ends of the main guidewire section and the extension section to hold the sections in axial alignment including an open-ended, internally threaded female member on a mating end of one of the guidewire sections and a threaded female connecting member on the mating end of the other guidewire section which is adapted to be inserted into and threadably engaged with the male connecting member to releasably secure the two sections together, at least one of said connecting members being fixed to a mating end of a section and free to rotate with respect thereto.

2. The extendable guidewire system of claim 1 wherein the female member is fixed to the distal end of the guidewire extension section and the male member is on the proximal end of the main guidewire section.

3. The extendable guidewire system of claim 1 wherein the female member is rotatably mounted about the distal end of the guidewire extension section.

4. The guidewire extension system of claim 1 wherein the female member is fixed to an enlarged end of a guidewire section by an internal collar bonded thereto which has an internal diameter smaller than the maximum dimension of the enlarged end.

* * * * *

UNITED STATES PATENT AND TRADEMARK OFFICE
CERTIFICATE OF CORRECTION

PATENT NO. : 4,966,163
DATED : October 30, 1990
INVENTOR(S) : Jeffrey L. Kraus and Linda T. Guthrie It is certified that error appears in the above-identified patent and that said Letters Patent is hereby corrected as shown below:

Column 1, line 27 "an" should read -- and --.

Column 1, line 47 "no" should read -- not --.

Column 4, line 13 "wither" should read --either--.

Column 4, line 38 --mating end; and-- should follow "having a"

Column 4, line 43 --connecting-- should follow "female"

Column 4, lines 44-45 "threaded female" should read -- threaded male --

Column 4, line 47 "male" should be --female--

Signed and Sealed this

Fifth Day of May, 1992

Attest:

DOUGLAS B. COMER

*Attesting Officer*     Acting Commissioner of Patents and Trademarks